(12) United States Patent
Potter et al.

(10) Patent No.: US 6,677,383 B1
(45) Date of Patent: Jan. 13, 2004

(54) HYDROXYLATION ACTIVATED PRODRUGS

(75) Inventors: Gerard Andrew Potter, Leicester (GB); Lawrence Hylton Patterson, Leicester (GB); Michael Danny Burke, Leicester (GB); Paul Crispin Butler, Leicester (GB)

(73) Assignee: De Montfort University, Leicester (GB)

( * ) Notice: Subject to any disclaimer, the term of this patent is extended or adjusted under 35 U.S.C. 154(b) by 0 days.

(21) Appl. No.: 09/633,699

(22) Filed: Aug. 7, 2000

Related U.S. Application Data

(63) Continuation of application No. PCT/GB99/00155, filed on Feb. 2, 1999, which is a continuation of application No. 09/115,015, filed on Jul. 14, 1998, now Pat. No. 6,214,886.

(30) Foreign Application Priority Data

Feb. 6, 1998 (GB) .............................. 9802522

(51) Int. Cl.$^7$ ......................... A61K 31/09; G01N 33/48

(52) U.S. Cl. ..................... 514/720; 514/721; 436/64; 435/156; 568/646

(58) Field of Search ................................ 568/579, 646, 568/660, 644, 630, 63; 546/330; 514/689, 646, 715, 805, 708, 720, 721; 436/64; 435/132, 184, 344, 156

(56) References Cited

U.S. PATENT DOCUMENTS

| | | | |
|---|---|---|---|
| 5,276,058 A | 1/1994 | Satoh et al. | 514/646 |
| 5,287,386 A | 2/1994 | Wade et al. | 375/36 |
| 5,430,062 A | * 7/1995 | Cushman et al. | 514/546 |
| 5,471,170 A | 11/1995 | Genest | 330/151 |
| 5,773,435 A | 6/1998 | Kadow et al. | 514/214 |
| 5,966,032 A | 10/1999 | Elrabaa et al. | 326/84 |
| 6,214,886 B1 | 4/2001 | Potter et al. | 514/685 |
| 6,346,550 B2 | 2/2002 | Potter et al. | 514/685 |
| 2002/0037296 A1 | 3/2002 | Potter et al. | 424/400 |

FOREIGN PATENT DOCUMENTS

| | | | |
|---|---|---|---|
| CA | 2109259 | 4/1994 | C07H/15/26 |
| DE | 43 09 344 A1 | 3/1993 | A61K/31/66 |
| DE | 42 36 237 A1 | 4/1994 | C07H/15/04 |
| EP | 0322738 | 12/1988 | |
| EP | 0 322 738 A2 | 7/1989 | A61K/31/165 |
| EP | 0 642 799 A1 | 3/1995 | A61K/47/48 |
| WO | 9712246 | 4/1997 | G01N/33/574 |
| WO | WO 99/40944 | 8/1999 | A61K/47/48 |

OTHER PUBLICATIONS

Cushman et al, Synthesis and Evaluation of Analogues of (Z)–1–(4–Methoxyphenyl)–2–(3,4,5–trimethoxyphenyl)ethene as Potential Cytotoxic and Antiitotic Agents, J. med. Chem., 1992, 35 p. 2293–2306.*

Murray et al, Tumor–specific expression of cytochrome P450 CYP1B1, 1997, Cancer Research, vol. 47 iss. 14 pp 3026–3031. see abstract and citation. AN 1997:477786 CAPLUS.*

"Combretastatin A–4$^1$, an Agent that Displays Potent and Selective Toxicity toward Tumor Vasculature"; by Dark et al. (Cancer Research pp. 1829–1834.).

"Induction of Apoptosis in Proliferating Human Endothelial ells by Tumor–Specific Antiangiogenesis Agent Combretastatin A–4$^{1}$" by Iyet et al. (Cancer Research 58, pp. 4510–4514).

Luch A et al., "Stable Expression of Human Cytochrome P450 1B1 in V79 Chinese Hamster Cells and Metabolically Catalyzed DNA Adduct Formation of Dibenzo[a,l ]pyrene", Chem Res. Toxicol. 11 pp. 686–695, (1998).

Tully et al., "Preparation of cyclomanganated chalcones and their reactions with methyl acrylate and other α, β–unsaturated carbonyl compounds", J. Organometallic Chem 503(1): pp. 75–92, (1995).

Klein, *Chemical Abstracts*, The American Chemical Society, Vol 120, No. 1, Abstract 14,657c, pp. 422, (1994).

Won C.M., "Kinetics and mechanism of hydrolysis of tryphostins", International Hournal of Pharmaceutics, vol. 104(1), pp. 29–40, (1994).

Doechmer J et al., "Chinese Cells Genetically Engineered for Stable Expression f Cytochromes P450", Meth. Enzymol, vol. 206, pp. 117–122, (1991).

Carmichael J. et al., Cancer Res. Vol 47, pp. 936–942, (1987).

Gutsche et al., *Chemical Abstracts*, The American Chemical Society, Vol 53, No. 9, Abstract 9122, (1959).

Patterson LH et al., 1998, XP–002106818. "Reductive Metabolism: its Application in Prodrug Activation" *Biomed. Health Res.* 25:72–79.

Chang TK et al., 1993, "Differential Activation of Cyclophosphamide and Ifosphamide by Cytochromes P–450 2B and 3A in Human Liver Microsomes" *Cancer Res.* 53(23):5629–5637 [Chemical Abstracts 120:94956].

Barrie et al., 1989, "Inhibition of 17α–Hydroxylase/ C17–C20 Lyase By Bifluranol And Its Analogues" *J. Steroid Biochem*. 33(6):1191–1195.

Eckert H et al., 1987, "Triphosgene, a Crystalline Phosgene Substitute" *Agnew, Chem. Int. Ed. Engl.* 26(9):894–895.

1978, "I.26 Fractional Distillation At Atmospheric Pressure" *Vogels Textbook of Practical Organic Chemistry*, 4th Ed. 878:146–155.

McMurray JE et al., 1974, "Electron Spin Resonance Studies on Diol Dehydrase" *J. Am. Chem. Soc.* 96(14):4708–9.

Wittig G, et al., 1973, "Methylenecyclohexane" *Org. Synth. Coll.* 5:751–754.

(List continued on next page.)

*Primary Examiner*—Rosalynd Keys
(74) *Attorney, Agent, or Firm*—Baker Botts L.L.P.

(57) ABSTRACT

The present invention concerns enzymatic aromatic hydroxylation-activated prodrugs, particularly anti-tumor prodrugs and those which are specifically activated by the hydroxylation activity of the enzyme CYP1B1.

5 Claims, 1 Drawing Sheet

OTHER PUBLICATIONS

"Synthesis and Evaluation of Analogues of (Z)–1–(4–Methoxyphenyl)–2–(3,4,5,–trimethoxyphenyl)ethene as Potential Cytotoxic and Antimitotic Agents" by Cushman et al.; J.Med.Chem. 1992, 35, pp. 2293–2306 (XP 000571677).

"Antineoplastic Agents 322. Synthesis of combretastatin A–4 prodrugs" by Pettit et al.; Anti–Cancer Drug Design (1995), 10, pp. 299–309, Oxford University Press; (XP–002102893).

Patent Abstracts of Japan 08188546.

"Polyhydroxylated Phenylacrylic Acid Derivatives as new Anti–tumor Agents" by Hussoin et al.; Journal of Pharmaceutical Sciences, vol. 80, No. 5, May 1991 pp. 416–418 (XP–002102894).

Patent Abstracts of Japan 61076433.

XP–002102896; 5001 Chemical Abstracts, vol. 68, 1968, No. 5, p. 2014.

"Novel Combretastatin Analogues Effective against Murine Solid Tumors: Design and Structure–Activity Relationships" by Ohsumi et al. (XP–002102895) J.Med. Chem. 1998, 41, 3022–3032.

"Potent Antimitotic and Cell Growth Inhibitory Properties of Substituted Chalcones" by Ducki et al; Bioorganic & Medicinal Chemistry Letters 8 (1998) 1051–1056.

* cited by examiner

HYDROXYLATION ACTIVATED PRODRUGS

CROSS-REFERENCE TO RELATED APPLICATIONS

This application is a continuation of International Application No. PCT/GB99/00155, which was filed on Feb. 2, 1999 and which published in English on Aug. 12, 1999, which in turn claims priority from U.K. Application No. GB 9802522.4, which was filed on Feb. 6, 1998, and a continuation of U.S Application No. 09/115,015, which was filed on Jul. 14, 1998 now U.S. Pat. No. 6,214,886.

The present invention concerns enzymatic aromatic hydroxylation-activated prodrugs. particularly anti-tumour prodrugs and those which are specifically activated by the hydroxylation activity of the enzyme CYP1B1.

Many conventional cytotoxic drugs are known which can be used for chemotherapeutic purposes. However. they typically suffer from the problem that they are generally cytotoxic and therefore may affect cells other than those which it is wished to destroy. This can be alleviated somewhat by using targetted drug delivery systems, for example direct injection to a site of tumourous tissue, or by e.g. binding the cytotoxic agent to antibody which specifically recognises an antigen displayed by cancerous cells. Alternatively, electromagnetic radiation may be used to cause chemical changes in an agent at a desired site in the body such that it becomes cytotoxic. However, all of these techniques have, to a greater or lesser extent, certain limitations and disadvantages.

It has been reported (Murray, G. I. et al., Jul. 15, 1997. Cancer Research, 57: 3026–3031) that the enzyme CYP1B1, a member of the cytochrome P450 family of xenobiotic metabolizing enzymes, is expressed at a high frequency in a range of human cancers including cancers of the breast, colon, lung, oesophagus, skin, lymph node, brain and testis, and that it is not detectable in normal tissues. This led to the conclusion (p. 3030, final sentence) that " . . . the expression of CYP1B1 in tumour cells provides a molecular target for the development of new anticancer drugs that could be selectively activated by the presence of CYP1B1 in tumour cells". No specific anticancer drugs are suggested.

The present inventors have now succeeded in creating a range of prodrugs which have little or negligible cytotoxic effect when in their normal state, but which are highly cytotoxic (i,e. have a substantially increased cytotoxicity) when hydroxylated by CYP1B1. This provides for a self-targetting drug delivery system in which a non-cytotoxic (or at leat negligibly cytotoxic) compound can be administered to a patient, for example in a systemic manner, the compound then being hydroxylated at the site of tumour cells (intratumoural hydroxylation) to form a highly cytotoxic compound which acts to kill the tumour cells. The fact that CYP1B1 is not expressed by normal cells means that the hydroxylation of the compound only occurs at the site of tumour cells and therefore only tumour cells are affected, thus providing a self-targetting drug delivery system.

The prodrugs of the present invention have the distinct advantage of being useful in the treatment of tumours at any site in the body, meaning that even tumours which have undergone metastasis (which are not normally susceptible to site-specific therapies) may be treated, as well of course as primary and secondary tumours.

According to the present invention there is provided a prodrug activated by enzymatic aromatic hydroxylation and having the formula (I):

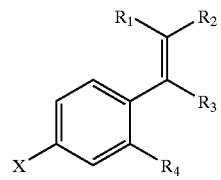

wherein:

X=H, OH or OMe;

$R_1$=H, $C_{1-4}$ lower alkyl, CN or Ar;

$R_2$=H, CN, $CONH_2$, $CSNH_2$. COAr or Ar; and

Ar=phenyl, pyridyl or substituted aryl;

and:

$R_3$=H or $C_{1-4}$ lower alkyl; and $R_4$=H, OH or OMe;

or:

$R_3,R_4$=$(CH_2)_n$, n=2, 3 or 4

The prodrug may be an anti-tumour prodrug. Examples of tumours include cancers (malignant neoplasms) as well as other neoplasms e.g. "innocent" tumours. The prodrug may be activated by hydroxylation by CYP1B1.

These prodrugs are styrene- or calchone-derivatives and their specific anti-tumour use is neither suggested nor disclosed by Murray, G. I. et al. (supra), nor is the fact that they are in fact prodrugs having an "activated" hydroxylated form. Where compounds of formula (I) have been previously identified and made, they have not been identified as anti-tumour agents due to their poor (or negligible) cytotoxicity. Thus the intratumoural hydroxylation of the prodrugs of the present invention provides them with a surprising and unexpected efficacy.

The styrene sub-structure of the compounds of formula (I) is essential in providing their efficacy. The Ar group may, for example, be a substituted aryl comprising 4-methoxyphenyl, 4-nitrophenyl, 3,5-dihydroxyphenyl or 3,4,5-trimethoxyphenyl, although other substituted aryls are, of course, also possible.

X may be hydroxy or methoxy.

As specified in formula (I) $R_3$ an $R_4$ may together form an alkyl chain having 2–4 carbon atoms, and thus may form part of a cycloalkyl group having 5,6 or 7 carbon atoms.

The prodrug may have the formula of any one of formulae (II)–(V):

(II):

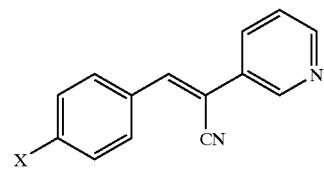

(III):

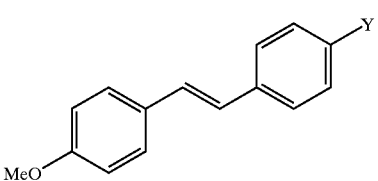

(VI):

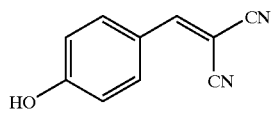

(V):

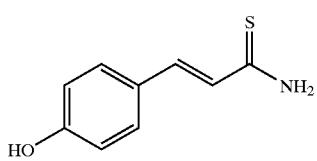

wherein X=OMe or OH, and Y=NO₂ or OMe.

Alternatively, the prodrug may have the formula of either one of formulae (VI) or (VII):

(VI):

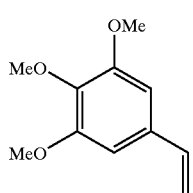

(VII):

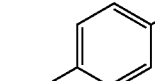

Alternatively the prodrug may have the formula of any one of formulae (VIII)–(XII):

(VIII):

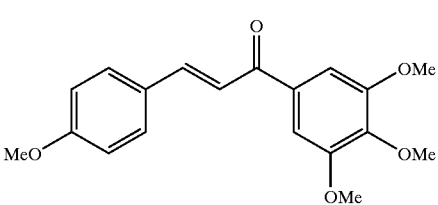

(IX):

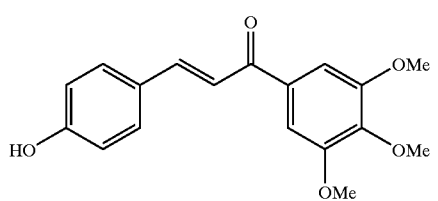

(X):

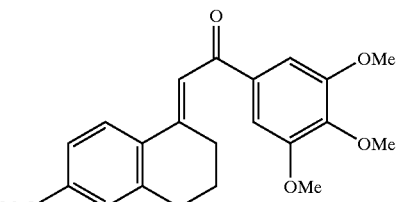

(XI):

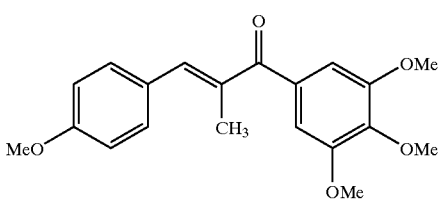

(XII):

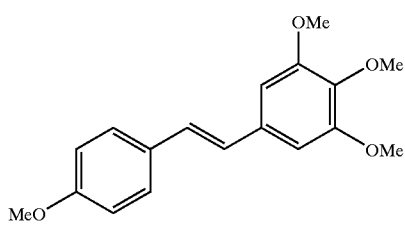

Hydroxylated forms of compounds (II)–(V) are potent tyrosine kinase inhibitors, and hydroxylated forms of compounds (VI) and (VII) are potent antimitotic agents. Previously, tyrosine kinase inhibitors have been of little chemotherapeutic benefit since the tyrosine kinase enzymes are ubiquitous in both normal and tumour cells and are thus not in themselves tumour-specific. However, the targetted production of tyrosine kinase inhibitor in tumour cells means that the inhibitory action will be specific to tumour cells. Furthermore, since the inhibitory activity will only be found in tumour cells, the tyrosine kinase inhibitor itself need not be isoform specific for a particular tyrosine kinase enzyme since any inhibition of tyrosine kinase activity will contribute to tumour inhibition and cell destruction.

Similarly, the antimitotic prodrugs of formulae (VI) and (VII) and (VIII)–(XII) are particularly useful since present antimitotic agents are of limited use due to the severe side-effects resulting from the poisoning of both normal and tumour cells. The present invention however allows for the specific in situ generation of the antimitotic agent at tumour cells, resulting in their specific targetting.

Methods of synthesis of the prodrugs of the present invention will be readily apparent to one skilled in the art, for example as exemplified below. The compounds of the invention may be prepared in a variety of different ways, for example by aldol condensation (Vogels Textbook of Practical Organic Chemistry, 4th Edition, p.146), by McMurry coupling (McMurry and Fleming, 1974, J. Am. Chem. Soc., 96: 4708–4709), or by the Wittig reaction (1973, Org. Synth. Coll., 5: 751).

Also provided according to the present invention is a prodrug according to the present invention for use in a method of treatment or diagnosis of the human or animal body, particularly the treatment or diagnosis of tumours.

Also provided according to the present invention is the use of a prodrug according to the present invention in the manufacture of a medicament for the treatment of tumours.

Also provided according to the present invention is a method of manufacture of a medicament, comprising the use of a prodrug according to the present invention. The medicament may be for the treatment of a tumour.

Also provided according to the present invention is a method of treatment or diagnosis of a tumour in a patient, comprising administering to the patient a prodrug according to the present invention.

Methods of manufacture of medicaments are well known. For example a medicament may additionally comprise a pharmaceutically acceptable carrier, diluent or excipient (Reminton's Pharmaceutical Sciences and US Pharmacopeia, 1984, Mack Publishing Company, Easton, Pa., USA).

The exact dose (i.e. a pharmaceutically acceptable dose) of prodrug to be administered to a patient may be readily determined by one skilled in the art, for example by the use of simple dose-response experiments.

Since the prodrugs of the present invention are specific to tumour cells, they may not only be used to treat tumours, but may also be used to determine whether or not a patient (or a sample taken from a patient) has tumour cells. For example, cell numbers in a sample may be assayed, as may the presence and quantity of the hydroxylated prodrug, thus providing for the diagnosis of the presence of tumour cells.

Also provided according to the present invention is the hydroxylated form of a prodrug according to the present invention.

The invention will be further apparent from the following description, which shows, by way of example only, forms of prodrugs.

BRIEF DESCRIPTION OF DRAWING

The FIGURE shows the results of a 40 hour exposure of cells to the compound (VII) (also referred to as DMU 102). X-axis shows the concentration in $\mu M$ of DMU 102. Y-axis shows the survival rate for cells, as a percentage of surviving cells in a control experiment. Error bars shows results ±1 SE (standard error). Circular markers are for cell line V79 mz. Triangular markers are for cell line V79h1B1.

EXPERIMENTAL

Figure 1:
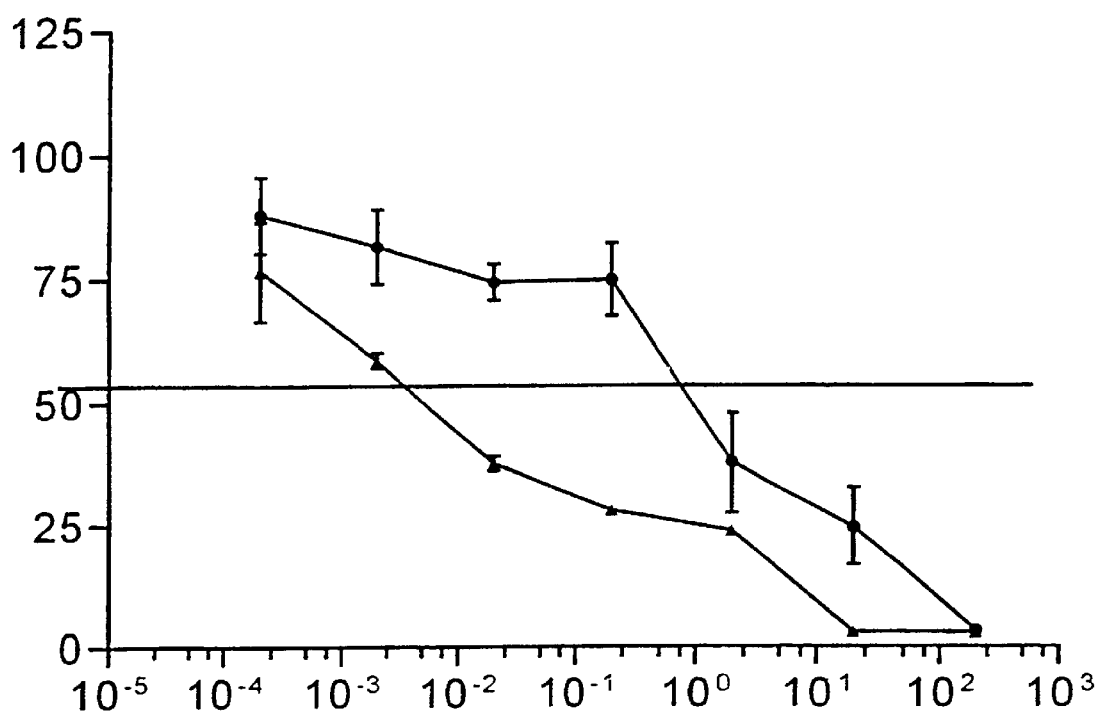

Prodrugs according to the present invention were synthesised as described below and the products of their hydroxylated metabolites assayed for the presence of the desired hydroxylation products. Their in vitro cytotoxicity against control and test cell lines was also determined.

Microsomal Preparation of Resected Human Tumour Tissue

A microsomal preparation of human tumour tissue expressing the CYP1B1 enzyme was prepared essentially as described by the method of Barrie et al. (1989. J. Steroid Biochem., 6: 1191–1195)

Metabolism Studies

Experiment were carried out at 37° C., under yellow light.

An array of 1.5 ml centrifuge tubes were set up in a water bath shaker under aerobic conditions. To each tube was then added 500 $\mu l$ of pH 7.6 buffer (0.1 M $NaK_2PO_4$), followed by NADPH (5 $\mu l$ of a 25 mM stock solution). The microsomal preparation (80 $\mu l$) was then added and the tubes preincubated for 5 minutes at 37° C. The prodrug substrate was then added (10 $\mu l$ of a 5 mM stock solution) and incubated for 1 hour at 37° C. After 1 hour the tubes were transferred to an ice/water cooling bath (0° C.). The tubes were then centrifuged at 1 5,000 rpm for 30 minutes. A sample of the supernatant (100 $\mu l$) was then taken and analysed by HPLC.

HPLC conditions: Spherisorb C18 (25 cm×4.6 mm id), used without guard column. Flow rate 1 ml/min. Eluent 75% 0.1 M $KH_2PO_4$ and 25% acetonitrile.

The prodrugs were assayed as described above and were found to undergo aromatic hydroxylation. The hydroxylated metabolite was detected by HPLC, and confirmed by synthesis of the authentic hydroxylated metabolite.

Compound IIa (below), (Z)-1-Cyano-1-(3-pyridyl)-2-(4-methoxyphenyl)ethene, was converted to the hydroxylated metabolite (Z)-1-Cyano-1-(3-pyridyl)-2-(3-hydroxy-4-methoxyphenyl)ethene.

Compound IIIc, (E)-(3,4',5)-trihydroxystilbene was converted to the hydroxylated metabolite (E)-(3,3',4,5')-tetrahydroxystilbene.

Compound VII (E)-1-(4-Methoxyphenyl)-3-(3,4,5-trimethoxyphenyl)prop-1-en-3-one was converted to the hydroxylated metabolite (E)-1-(3-Hydroxy4-methoxyphenyl)-3-(3,4,5-trimethoxyphenyl)prop-1-en-3-one.

In vitro Cytotoxicity Studies

The cytotoxicity assay method used was a modification of the MTT cytotoxicity assay (Carmichael et al., 1987, Cancer Research, 47: 936). The activity of the compounds were evaluated in cell lines which express the enzyme CYP1B1 (V79mzhu1B1) and the corresponding parental cell line which does not express CYP1B(V79mz) (Luch et al., 1998, Chem. Res. Toxicol., 11: 686). $10^3$ cells were plated in 100 $\mu l$ DMEM (high glucose) (Dulbecco's Modified Eagles Medium, Life Science International) plus 10% heat-inactivated FBS (Foetal Bovine Serum. Hybrimax, Sigma.) per well of 96 well (Nunc) microtitre plates for 24 hours-to allow adherance and metabolic recovery followed by addition in quadruplicate of compound at double strength in the same medium in 100 $\mu l$ to give a final maximal concentration of 0.2% DMSO (dimethyl sulfoxide). Compound stocks were made up as 100 mM in DMSO and stored for no more than one month at 4° C. The plates were then incubated at 37° C., 5% $CO_2$, 100% humidity for a further 48 hours followed by washing by immersion 3 times in Dulbecco's PBS (phosphate buffered saline) A. 50 $\mu l$ of RPMI 1640 w/o phenol red (Roswell Park Memorial Institute Medium 1640, Life Science International) with 2 mg/ml MTT was then added for four hours as above, excess MTT removed by aspiration and 125 $\mu l$ of DMSO added on a vortex for 30 minutes to solubilize the product. The absorbance at $A_{450}$ was recorded and the results expressed as a % survival of carrier only treated controls. From this data was calculated the IC50 value, which is the concentration at which 50% cytotoxicity is observed. Confirmation of expression of CYP1B1 was determined by immunocytology, Western blotting and EROD assay (ethoxyresorufin-O-dealkylase assay; Burke, M. D. et al., 1985, Biochem. Pharmacol., 34: 3337) of cells used in the assay at the time point when the compounds were added, either fixed in methanol at −20° C., or harvested from replicate plates and stored at −80° C. until assay.

The prodrugs were evaluated using the above assay system, and the results are shown in Table 1. These results demonstrate that the compounds of this invention exhibit differential toxicity against the CYP1B1 expressing cell line.

TABLE 1

Growth Inhibition of Cells not Expressing and Expressing CYP1B1 ($IC_{50}$/uM ± 2%)

| Compound | DMU Code No. | V79 Cells | V791B1 Cells |
| --- | --- | --- | --- |
| Compound IIa | DMU-201 | 1.81 | 1.63 |
| Compound IIIb | DMU-205 | 58.2 | 8.3 |
| Compound VII | DMU-102 | 1.0 | 0.005 |
| Compound VIII | DMU-116 | 1.81 | 1.71 |

Of particular note is the discovery that compound VII is around 200-fold more cytotoxic to the cell line expressing CYP1B1 than to the parental cell line not expressing this enzyme. Therefore compound VII is particularly useful as a tumour selective anticancer agent. A plot of % cell survival versus concentration for compound VII (DMU-102) is shown in FIG. 1.

Methods of Synthesis

Compound IIa (Z)-1-Cyano-1-(3-pyridyl)-2-(4-methoxyphenyl)ethene (DMU-201)

To a stirred mixture of 4-methoxybenzaldehyde (2 g, 14.69 mmol) and 3-pyridylacetonitrile (1.58 ml, 14.84 mmol) in methanol (30 ml) was added 50% w/v sodium hydroxide (1 ml). The reaction was stirred for 3 hours. The reaction mixture was quenched with water (20 ml), acidified with 2N HCl, then rebasified with dilute NaOH (aq), and the reaction product was extracted successively into dichloromethene (3×20 ml). The organic solutions were dried over anhydrous $MgSO_4$ and the solvent removed. Purification by column chromatography ($SiO_2$, Hexane/Ethylacetate 8:2; 1:1) gave 2.01 g (58% yield) of the title compound as a straw coloured solid: 1H-NMR (CDCl3) 8.80 (d, 1H), 8.50 (m, 1H), 7.80 (m, 3H), 7.45 (s, 1H), 7.25 (m, 1H), 6.90 (m, 2H), 3.80 (s, 3H). 13C NMR (CDCl3) 161.9, 157.6, 157.5, 149.5, 146.9, 143.3, 133.1, 131.4, 130.9, 126, 123.5, 117.7, 114.5, 105.2, 55.4. Mass Spectrum m/e (M+1) 237.

Hydroxylated Metabolite of Compound IIa (Z)-1-Cyano-1-(3-pyridyl)-2-(3-hydroxy-4-methoxyphenyl)ethene (DMU-202)

A mixture of 4-methoxy-3-hydroxybenzaldehyde (0.5 g, 3.3 mmoles), 3-pyridylacetonitrile (0.35 ml, 3.3 mmoles) and 50% w/v of aqueous NaOH (3 ml) in methanol (10 ml) was stirred at room temperature for 30 minutes. The yellow solid that precipitated was filtered, washed with cooled methanol (1 ml), cooled $CH_2Cl_2$ (5 ml) and dried under vacuum over $P_2O_5$ to yield 0.5 g (60%) of the title compound as a yellow solid. 1H-NMR (CD3OD) 8.8 (m, 1H), 8.5 (m, 1H), 8.1 (m, 1H), 7.7 (s, 1H), 7.5 (m, 1H), 7.3 (d, 1H), 7.2 (d, 1H), 6.8 (d, 1H). Mass Spectrum m/e (M+1) 253.

Compound IIb (Z)-1-Cyano-1-(3-pyridyl)-2-(4-hydroxyphenyl)ethene (DMU-208)

A mixture of 4-hydroxybenzaldehyde (0.5 g, 4.1 mmoles), 3-pyridylacetonitrile (0.54 ml, 4.1 mmoles) and 50% w/v of aqueous NaOH (3.3 ml) in methanol (10 ml) was stirred at room temperature for 30 minutes. The yellow precipitate that formed was filtered, washed with cooled methanol (1 ml), cooled $CH_2Cl_2$ (10 ml), and dried under vacuum over $P_2O_5$ to yield 0.6 g (66%) of the title compound. 1H-NMR (CD3OD) 8.8 (d, 1H), 8.4 (m, 1H), 8.05 (m, 1H), 7.8 (m, 2H), 7.6 (s, 1H), 7.4 (m, 1H), 6.6 (m, 2H). 13C-NMR (DMSO) 177.52, 175.57, 146.59, 145.06, 144.78, 133.15, 132.73, 130.97, 123.8, 120.8, 120.3, 114.3, 88.5; Mass Spectrum m/e (M+1) 223.

Compound IIIb (via McMurry Coupling)

(E)-(4,4')-Dimethoxystilbene (DMU-205)

$LiAlH_4$ (0.5 g, 13.18 mmoles) was added to a stirred slurry of $TiCl_3$ (3.13 g, 26.35 mmol) under $N_2$ in dry THF (20 ml). An instantaneous reaction occurred, accompanied by the evolution of heat and gas and by a rapid change of colour to deep black. A THF solution of 4-methoxybenzaldehyde (1.79, 13.18 mmoles) was then added. The mixture was refluxed for 4 hours. The reaction was quenched with cooled $H_2O$ (2 ml), extracted into ethylacetate (5×20 ml) and purified by column chromatography. $^1$H NMR (CDCl$_3$) δ 7.2 (4H, m), 6.8 (4H, m), 6.5 (2H, s), 3.7 (6H, s); Mass Spectrum (FAB) m/e (M+1) 241.

Hydroxylated Metabolite of Compound IIIb (via Wittig Reaction)

(E)-3-Hydroxy-4,4'-dimethoxystilbene

To a stirred mixture of 4-methoxybenzyltriphenylphosphonium chloride (5.51 g, 13mmol) and 4-methoxy-3-hydroxybenzaldehyde (2 g, 13 mmol) in $CH_2Cl_2$ was added a cooled aqueous solution of NaOH(62.5 eq) in $H_2O$. The mixture was stirred at room temperature for 48 h. The aqueous layer was then acidified to pH 5 and the precipitated solid was filtered and dried. Purification by silica gel chromatography using hexane/ethyl acetate (1:1) gave the title E-trans product as a colourless solid 0.11 g (3%): $^1$H NMR (DMSO) δ 9.3 (1H, bs). 7.6 (2H, d), 7.2 (7H, m), 3.5 (6H, s): Mass Spectrum (FAB) 257 (M+1).

Compound VII (E)-1-(4-Methoxyphenyl)-3-(3,4,5-trimethoxyphenyl)prop-1-en-3-one (DMU-102)

To a stirred solution of 4-methoxybenzaldehyde (1.0 g, 7.3 mmol) and 3,4,5-trimethoxyacetophenone (1.54 g, 7.3 mmol) in methanol (30 ml) was added a 50% w/v solution of aqueous NaOH (1 ml). The mixture was stirred for 24 h at room temperature, acidified with 2N HCl and extracted with ethyl acetate (3×30 ml). The combined organic phase was dried over anhydrous $MgSO_4$, filtered, and the solvent evaporated in vacuo. The product was purified by column chromatography followed by recrystallisation from methanol to afford the title compound as a pale yellow solid 1.22 g (51%). $^1$H NMR (CDCl$_3$) δ 7.8 (1H, d), 7.6 (2H, m), 7.4 (1H, d), 7.3 (2H, d), 7.0 (2H, d), 3.9 (9H, s), 3.8 (3H s). Mass Spectrum (FAB) m/e 329 (M+1).

Hydroxylated Metabolite of Compound VII (E)-1-(3-Hydroxy-4-methoxyphenyl)-3-(3,4,5-trimethoxyphenyl)prop-1-en-3-one To a stirred solution of 3-hydroxy-4-methoxybenzaldehyde (1.0 g, 6.57 mmol) and 3,4,5-trimethoxyacetophenone (1.38 g, 6.57 mmol) in methanol (30 ml) was added a 50% w/v solution of aqueous NaOH (1 ml). The mixture was stirred for 24 h at room temperature, acidified with 2N HCl, and extracted with ethyl acetate (3×30 ml). The combined organic phase was dried over anhydrous $MgSO_4$, filtered, and the solvent evaporated in vacuo. The product was purified by crystallisation from methanol (0.63 g, 28% yield). $^1$H-NMR(CDCl$_3$) δ 7.8 (1H, d), 7.3 (4H, m), 7.2 (1H, m), 6.9 (1H, d), 5.7 (1H, s), 3.9 (12H, s). Mass Spectrum (FAB) m/e 345 (M+1),

Compound XII (via Wittig Reaction)
(E)-3,4,5-Trimethoxy-4'-methoxystilbene (DMU-212)

To a stirred mixture of 4-methoxybenzyltriphenylphosphonium chloride (6.4 g, 15.3 mmol) and 3,4,5-trimethoxybenzaldehyde (3 g, 15.3 mmol) in CH$_2$Cl$_2$ was added a cooled aqueous solution of NaOH (62.5 eq) in H$_2$O. The mixture was stirred at room temperature for 48 hours. The organic phase was separated and the aqueous phase was washed with CH$_2$Cl$_2$. The organic phase was concentrated and the residue was recrystallised from ethanol to yield the title E-trans isomer. $^1$H NMR (CDCl$_3$) δ 8.7 (1H, d:), 8.2 (4H, m), 8.0 (2H, s), 5.2 (6H, s), 5.0 (6H, s). Mass Spectrum (FAB) 301 (M+1).

Compound VI
(Z)-3,4,5-Trimethoxy-4'-methoxystilbene (DMU-213)

The filtrate from the recrystallisation step following the preparation of Compound XII above was concentrated and purified by column chromatography using hexane/ethyl acetate (8:2) as eluant to give the title Z-cis isomer as a colourless solid 0.1 g (yield 7%). $^1$H NMR (CDCl$_3$) δ 7.2 (2H, m), 6.8 (2H, m), 6.5 (4H, m), 3.9 (3H, s), 3.8 (3H, s), 3.7 (6H, s). Mass Spectrum (FAB) 301 (M+1).

Compound VIII
(E)-1-(4-Hydroxyphenyl)-3-(3,4,5-trimethoxyphenyl)prop-1-en-3-one (DMU-116)

To a stirred solution of 4-hydroxybenzaldehyde (1.0 g, 8.19 mmol) and 3,4,5-trimethoxyacetophenone (1.72 g, 8.19 mmol) in methanol (30 ml) was added a 50% w/v solution of aqueous NaOH (1 ml). The mixture was stirred for 24 hours at room temperature, acidified with 2N HCl and extracted with ethyl acetate (3×30 ml). The combined organic phase was dried over anhydrous MgSO$_4$, filtered, and the solvent evaporated in vacuo. The product was purified by column chromatography using hexane/ethyl acetate (7:3) as eluent to afford the title compound as a pale yellow solid (0.125 g, 5%). $^1$H-NMR (CDCl$_3$) δ 7.8 (1H, d), 7.6 (2H, m), 7.4 (1H, s), 7.25 (2H, m), 6.9 (2H, d), 5.6 (1H, bs) 3.95 (9H, s). Mass Spectrum (FAB) m/e 315 (M+1).

Compound IX
(E)-1-(2,4-Dimethoxyphenyl)-3-(3,4,5-trimethoxyphenyl)prop-1-en-3-one (DMU-132)

To a stirred solution of 2,4-dimethoxybenzaldehyde (1 g, 6.00 mmol) and 3,4,5-trimethoxyacetophenone (1.27 g, 6.00 mmol) in methanol (30 ml) was added a 50% w/v solution of aqueous NaOH (1 ml). The mixture was stirred for 24 hours at room temperature, acidified with 2N HCl and extracted with ethyl acetate (3×30 ml). The combined organic phase was dried over anhydrous MgSO$_4$, filtered, and the solvent evaporated in vacuo. The product was purified by recrystallisation from ethanol to afford the title compound as a pale yellow solid, 1.67 g (78%). $^1$H-NMR (CDCl$_3$) δ 8.0 (1H, d), 7.5 (1H, d), 7.4 (1H, d), 7.2 (2H, s), 6.6 (1H, dd), 6.5 (1H, d), 3.9 (9H, d), 3.85 (3H, s), 3.83 (3H, s). Mass Spectrum (FAB) m/e 359 (M+1).

Compound X (DMU-129)

To a stirred solution of 6-methoxy-1-tetralone (1.28 g, 7.3 mmol) and 3,4,5-trimethoxyacetophenone (1.54 g, 7.3 mmol) in methanol (30 ml) was added a 50% w/v solution of aqueous NaOH (1 ml). The mixture was stirred for 24 hours at room temperature, acidified with 2N HCl and extracted with ethyl acetate (3×30 ml). The combined organic phase was dried over anhydrous MgSO$_4$, filtered, and the solvent evaporated in vacuo. The product was purified by column chromatography, followed by recrystallisation from ethanol to afford the title compound 0.25 g (9%). $^1$H NMR (CDCl$_3$) δ 7.4 (1H, s), 7.1–7.3 (5H, m), 3.9 (9H, s), 3.8 (3H, s), 1.6–2.3 (6H, complex m). Mass Spectrum (FAB) m/e 369 (M+1).

Compound XI (DMU-122)
(E)-1-(4-Methoxyphenyl)-2-methyl-3-(3,4,5-trimethoxyphenyl)prop-1-en-3-one To a stirred solution of 4-methoxybenzaldehyde (1.0 g, 7.3 mmol) and 1-(3,4,5-trimethoxyphenyl)propan-1-one (1.64 g, 7.3 mmol) in methanol (30 ml) was added a 50% w/v solution of aqueous NaOH (1 ml). The mixture was stirred for 24 hours at room temperature, acidified with 2N HCl and extracted with ethyl acetate (3×30 ml). The combined organic phase was dried over anhydrous MgSO$_4$, filtered, and concentrated in vacuo. The product was purified by column chromatography using hexane/ethylacetate (4:1) as eluant, followed by recrystallisation from ethanol to afford the title compound as a pale yellow solid, 0.36 g (14%). $^1$H-NMR (CDCl$_3$) δ 7.8 (1H, s), 7.6 (2H, m), 7.3 (2H, d), 7.0 (2H, d), 3.9 (9H, s), 3.8 (3H, s), 2.3 (3H, s). Mass Spectrum (FAB) m/e 343 (M+1).

What is claimed is:

1. A method of inhibiting growth of tumor cells containing an aromatic hydroxylase enzyme comprising contacting the tumor cells with a prodrug having the formula:

(XII):

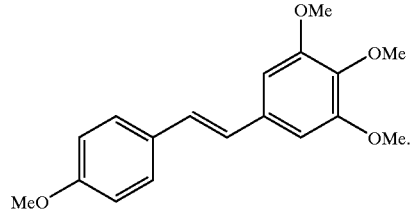

2. A method according to claim 1 wherein the aromatic hydroxylase enzyme is CYP1B1.

3. A method of determining the presence of tumor cells containing an aromatic hydroxylase enzyme in a cell sample, the method comprising contacting the cell sample with a compound having the formula (XII)

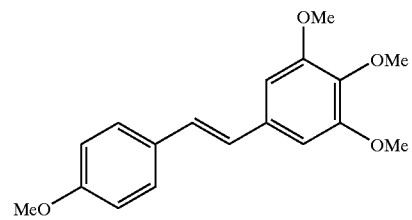

to form a hydroxylated metabolite of the compound in tumor cells containing the aromatic hydroxylase enzyme and determining the presence or absence of the hydroxylated metabolite of the compound wherein the presence of the hydroxylated metabolite in the cell sample indicates the presence of tumor cells in the cell sample.

4. A method according to claim 3 further comprising determining the amount of hydroxylated metabolites of the compound present in the cell sample.

5. A method according to claim 3 further comprising determining the number of cells in the cell sample.

* * * * *

UNITED STATES PATENT AND TRADEMARK OFFICE
CERTIFICATE OF CORRECTION

PATENT NO. : 6,677,383 B1
DATED : January 13, 2004
INVENTOR(S) : Potter et al.

It is certified that error appears in the above-identified patent and that said Letters Patent is hereby corrected as shown below:

Title page,
Item [56], References Cited, OTHER PUBLICATIONS, "Cushman et al," reference, "Antiitotic" should read -- Antimitotic --; "Luch A et al.," reference, "Dibenzo[a,l ] pyrene" should read --Dibenzo[α,l]pyrene --; "Won C.M.," reference, "Hournal" should read -- Journal --; and "Doechmer J et al.," reference, "f" should read -- of --

Column 1,
Line 10, "U.S" should read -- U.S. --
Line 46, "i,e." should read -- i.e., --
Line 49, "leat" should read -- least --

Column 2,
Line 44, "an" should read -- and --
Line 46, "5,6" should read -- 5, 6 --

Column 5,
Line 59, "Experiment" should read -- Experiments --

Column 6,
Line 2, "1 5,000" should read -- 15,000 --
Line 22, "Hydroxy4-" should read -- Hydroxy-4- --
Line 38, "adherance" should read -- adherence --

Column 7,
Table 1, "uM" should read -- $\mu$M --
Line 36, "1H-NMR" should read -- $^1$H-NMR --; and "(CDC13)" should read -- (CDCl$_3$) --
Line 38, "13C NMR" should read -- $^{13}$C-NMR --
Line 38, "(CDCl3)" should read -- (CDCl$_3$) --
Lines 52-66, "1H-NMR" should read -- $^1$H-NMR --

Column 8,
Lines 17, 31 and 48, "$^1$H NMR" should read -- $^1$H-NMR --
Line 17, "(CDCl$_3$)" (CDC-numeral one-sub 3)" should read -- (CDCl$_3$) -- (CDC-lowercase "L"-sub 3) --
Line 24, "13mmol" should read -- 13 mmol --

UNITED STATES PATENT AND TRADEMARK OFFICE
CERTIFICATE OF CORRECTION

PATENT NO. : 6,677,383 B1
DATED : January 13, 2004
INVENTOR(S) : Potter et al.

It is certified that error appears in the above-identified patent and that said Letters Patent is hereby corrected as shown below:

Column 9,
Lines 11 and 20, "$^1$H NMR" should read -- $^1$H-NMR --

Column 10,
Line 3, "$^1$H NMR" should read -- $^1$H-NMR --

Signed and Sealed this

Twenty-ninth Day of June, 2004

JON W. DUDAS
*Acting Director of the United States Patent and Trademark Office*